Feb. 10, 1953 W. E. LAMMERTS Plant Pat. 1,167
ROSE PLANT
Filed Feb. 15, 1952
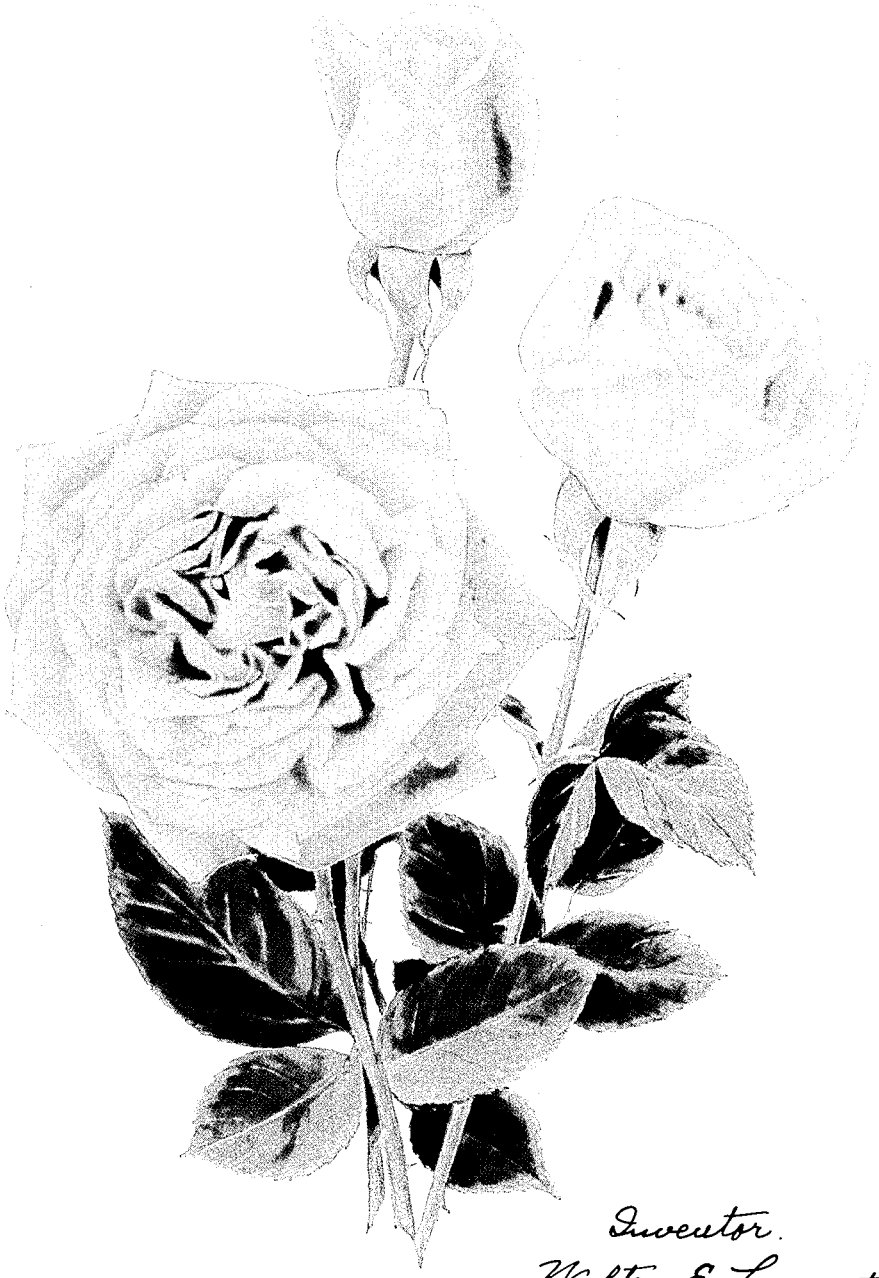
Inventor.
Walter E. Lammerts
By: Robert Robb
Attorneys.

Patented Feb. 10, 1953

Plant Pat. 1,167

UNITED STATES PATENT OFFICE 1,167

ROSE PLANT

Walter E. Lammerts, La Canada, Calif., assignor, by mesne assignments, to Germain's, Inc., Van Nuys, Calif., a corporation of California Application February 15, 1952, Serial No. 271,691

1 Claim. (Cl. 47—61)

The present invention relates to a new and distinct variety of rose plant of the hybrid tea class, originated by me by crossing the variety "Charlotte Armstrong" (Plant Patent No. 455) × the variety "Mirandy" (Plant Patent No. 632).

As the result of this cross, I have produced a new variety which is a very desirable improvement in red hybrid tea roses, combining the best features of both parents, yet distinct from each, as well as from all other varieties heretofore known in commerce.

In respect to its vigor of growth, my new variety falls between that of "Charlotte Armstrong" and "Mirandy," but it has a much more compact habit of growth than the former, and differs from both parents and from most other hybrid tea roses by its greater abundance of foliage which is retained clear to the base of the plant, even on older plants late in the season, this being a very unusual feature, and making a much better and more attractive appearance in the garden as a shrub.

The resistance of my new variety to mildew and blackspot is greater than that of "Mirandy," and although its resistance to mildew is not as pronounced as that of "Charlotte Armstrong," comparative tests in many Eastern gardens indicate that the resistance to blackspot is fully as great as that of "Charlotte Armstrong," particularly in the spring and early summer.

In respect to the form of the bud, my new variety resembles "Charlotte Armstrong" more than "Mirandy," and is an improvement over other red roses in that, except under the most adverse weather conditions, the bud is longer than "Mirandy," and more long-pointed to urn-shaped in form, resembling "Charlotte Armstrong" in this respect.

Another unusual feature and distinct improvement of my new variety is its predominant tendency to bear its flowers singly on sturdy, medium-long stems, which is ideal for an exhibition rose, whereas "Mirandy" usually bears its flowers two, three or four to the stem.

The greatest improvement in my new variety over "Mirandy" is that the buds do not "ball" nearly as much as "Mirandy" as the buds open during adverse cool, foggy weather, though my new variety is at its best in hot weather climates.

The color of the open flower of my new variety is very similar to that of "Mirandy," and is predominantly Chrysanthemum Crimson in general color effect, but to the eye, the color appears a lighter and more glowing red not readily defined by comparison with existing color charts. This very distinctive lighter and more iridescent glow is probably due to reflection from the satiny and velvety inside surface of the petals. A tendency to Rose Red shading also distinguishes the new variety from "Mirandy."

Asexual reproduction of my new variety by budding at La Canada, California, shows that the foregoing characteristics and distinctions come true to form and are established and transmitted through succeeding propagations.

The accompanying drawing shows typical specimens of my new variety, with the flowers and foliage in different stages of development, and with the colors depicted as nearly true as is possible in a color illustration.

The following is a detailed description of my new variety, with color terminology in accordance with the Horticultural Color Chart of the British Color Council, except where general color terms of ordinary dictionary significance are obvious:

Type: Hardy; dwarf; bush; outdoor; seedling; for garden decoration.

Class: Hybrid tea.

Breeding: Seedling.

*Seed parent.*—"Charlotte Armstrong."

*Pollen parent.*—"Mirandy."

Propagation: Holds its distinguishing characteristics through succeeding propagations by budding.

*Flower*

Locality where grown and observed: La Canada, California.

Flowers borne: Usually singly; rarely 2 or 3 to stem; on strong, medium-long stems.

Quantity of bloom: Free; abundant; outdoors.

Continuity: Continuous.

Fragrance: Centifolia.

Bud:

*Peduncle.*—Medium length; 2¼" to 3¾"; erect; stiff; medium green and heavily tinged with anthocyanin toward base; almost entirely smooth; few prickles and small thorns near base of peduncle of flowers on very vigorous stems only.

*Before calyx breaks.*—Size—medium large. Form—ovoid; without foliaceous appendages on the surface of the bud, but 3 of 5 sepals or every other sepal having small lateral lance-shaped appendages; with slender, much-cut foliaceous parts extending beyond the tip of the bud equal to one-fourth of its length on one sepal only. Color—Oxblood Red, Plate 00823, varying to Maroon, Plate 1030.

*As calyx breaks.*—Color—Chrysanthemum Crimson, Plate 824/1.

*As first petal opens.*—Size—large. Form—long ovoid; varying to urn-shaped at times in hot weather. Color:—Outside—Chrysanthemum Crimson, Plate 824/2 to 824/3; inside—near but not exactly Chrysanthemum crimson, Plate 824. Opening—is retarded from opening by cold weather, but opens up quite well even during cool, foggy weather, and in hot weather opens up very well.

Bloom:

*Size, when fully open.*—Large; 4 inches to 5 inches.

*Petalage.*—Very double; from 33 to 43 petals; arranged regularly.

*Form.*—Very high-centered at first; becoming cupped; petals at first tightly rolled inward; becoming later, at maturity, very loosely rolled outward, and inner or central petals on older flowers raising up and covering the stamens and petals.

Petals: Thick; soft; with inside satiny-velvety and outside dull.

*Shape.*—Outside — obovate; scalloped with apex with one notch; size—width 2" to 2⅜"; length 2" to 2⅛" with ⅓ of petals having ⅛" tip, but about ⅔ of petals with irregular indentation at apex instead of apical tip. Intermediate—lanceolate.

*Color.*—Rather uniform color throughout.

This description of a newly opened flower was made from a rose grown outdoors in the month of September, at La Canada, California:

*Color.*—Outside petal: outside surface—Chrysanthemum Crimson, Plate 824/2 to 824/3; inside surface—near (but not exactly) Chrysanthemum Crimson, Plate 824. Intermediate petal: outside surface—Spiraea Red, Plate 025; inside surface—Rose Red, Plate 724. Inner petal: outside surface—Spiraea Red, Plate 025; inside surface—Rose Red, Plate 724.

This description was made from a rose that was open for three days outdoors in the month of September, at La Canada, California:

*Color.*—Outside petal: outside surface—Tyrian Purple, Plate 727/3; inside surface—Tyrian Purple, Plate 727/2, tinged Rose Red, Plate 724, toward base. Inside petal: outside surface—Tyrian Purple, Plate 727/3. Inside surface—Tyrian Purple, Plate 727/2, tinged with Rose Red, Plate 724, toward base.

*General color effect.*—Newly opened flower—Rose Red, Plate 724, to Chrysanthemum Crimson, Plate 824/2. Three days open—Tyrian Purple, Plate 727/3, to Rose Red, Plate 724.

*Behavior*—Drop off cleanly; fading to Rose Red, Plate 724; very little affected by weather excepting that cold weather accelerates fading reaction to Rose Red, Plate 724.

*Flower longevity.*—On bush in garden—4 days in October. Cut roses grown outdoors, kept at living room temperatures—6 days in October.

*Reproductive organs*

Stamens: Medium number to many; arranged irregularly about pistils.

Filaments: Medium length; most with anthers. Color—Nasturtium Red, Plate 14/1.

Anthers: Small, open at various times. Color—Sulphur Yellow, Plate 1/2.

Pollen: Moderate. Color—Gold.

Pistils: Many; irregularly arranged.

Styles: Uneven; short; thin; irregularly bunched. Color—Light Red toward upper $\frac{1}{16}$ portion.

Stigma: Color—Pale Yellow to Cream.

Ovaries: All enclosed in calyx.

Hips: Globular with inconspicuous neck; smooth; walls thick, fleshy. Color—Persimmon Orange, Plate 710/2 shading to Jasper Red, Plate o18.

Sepals: Falling soon; moderate length; curled; recurved. Color—Olive Green.

*Plant*

Foliage:

*Leaves.*—Compound of 5 to 7 leaflets; medium size; leathery to semi-glossy.

*Leaflets.*—Shape — oval with apex acute; base round; margin simply serrate.

*Color.* — Mature: upper surface — Spinach Green, Plate o960/1; lower surface—Willow Green, Plate ooo862/1; veins conspicuously Anthocyanin Red. Young: upper surface—Sage Green, Plate ooo861; under surface — Scheeles Green, Plate 860/3, washed with Garnet Brown, Plate oo918/3.

*Rachis.* — Medium weight. Upper side — grooved; prickly. Under side — sparsely prickly.

*Stipules.*—Short; narrow; with points turning out at an angle of more than 45°.

*Disease.*—Resistant to mildew and blackspot, as determined by observation and comparison with other varieties, particularly "Mirandy."

Growth:

*Habit.*—Dwarf; bushy; much branched.

*Growth.*—Vigorous.

*Canes.*—Heavy.

*Main stems.*—Color—Fern Green, Plate o862, heavily tinged with Anthocyanin Red. Thorns—many; medium length; hooked downward; with narrow base; color—Garnet Brown, Plate oo918/3. Prickles—Many; color—Reddish Brown. Hairs—none.

*Branches.*—Color—Fern Green, Plate o862, shading to Oxblood Red, Plate oo823/3. Thorns—many; medium length; hooked downward; with short, narrow base; color — Oxblood Red, Plate oo823/2. Prickles—many; color—Reddish Brown. Hairs—none.

*New shoots.*—Color—Fern Green, Plate o862/2, shading to Rhodonite Red, Plate oo22. Thorns—many; short; hooked downward; with short, narrow base; color — Oxblood Red, Plate oo823/2. Prickles—many; color—Reddish. Hairs—none.

I claim:

A new and distinct variety of rose plant of the hybrid tea class, substantially as herein shown and described, characterized as to novelty particularly by its relatively vigorous and compact habit of growth, by its abundance of foliage and retention of the same clear to the base of the plant, even on older plants late in the season, by its resistance to mildew and blackspot, by its relatively long buds and the long-pointed to urn-shaped form of the same, by its predominant tendency to bear its flowers singly on sturdy, medium-long stems, by the reduced tendency of its buds to "ball" as they open during cool, foggy weather, and by the predominantly Chrysanthemum Crimson general color effect of its open flowers, but with an appearance to the eye of a lighter and iridescent glowing red color, and with a tendency to shadings of Rose Red.

WALTER E. LAMMERTS.

No references cited.